United States Patent
Lee et al.

(10) Patent No.: US 11,785,922 B2
(45) Date of Patent: Oct. 17, 2023

(54) RECOMBINANT VECTOR COMPRISING ERT2 FUSED TO CAS9

(71) Applicant: SEOUL NATIONAL UNIVERSITY HOSPITAL, Seoul (KR)

(72) Inventors: Eun Ju Lee, Seoul (KR); Hyo-Soo Kim, Seoul (KR)

(73) Assignee: SEOUL NATIONAL UNIVERSITY HOSPITAL, Seoul (KR)

( * ) Notice: Subject to any disclaimer, the term of this patent is extended or adjusted under 35 U.S.C. 154(b) by 935 days.

(21) Appl. No.: 16/624,575

(22) PCT Filed: May 3, 2018

(86) PCT No.: PCT/KR2018/005135
§ 371 (c)(1),
(2) Date: Dec. 19, 2019

(87) PCT Pub. No.: WO2018/236045
PCT Pub. Date: Dec. 27, 2018

(65) Prior Publication Data
US 2020/0128802 A1 Apr. 30, 2020

(30) Foreign Application Priority Data
Jun. 19, 2017 (KR) .................. 10-2017-0077221

(51) Int. Cl.
| | | |
|---|---|---|
| C12N 15/00 | (2006.01) | |
| C12N 15/113 | (2010.01) | |
| C12N 15/85 | (2006.01) | |
| C12N 15/09 | (2006.01) | |
| A01K 67/027 | (2006.01) | |
| C07K 14/72 | (2006.01) | |
| C12N 9/22 | (2006.01) | |

(52) U.S. Cl.
CPC .......... *A01K 67/0275* (2013.01); *C07K 14/72* (2013.01); *C12N 9/22* (2013.01); *C12N 15/113* (2013.01); *C12N 15/8509* (2013.01); *A01K 2217/07* (2013.01); *A01K 2227/105* (2013.01); *C07K 2319/09* (2013.01)

(58) Field of Classification Search
CPC .......... A01K 67/0275; A01K 2217/07; A01K 2227/105; A01K 2217/203; C07K 14/72; C07K 2319/09; C07K 2319/00; C07K 14/721; C12N 9/22; C12N 15/113; C12N 15/8509; C12N 2310/20; C12N 2830/205; C12N 15/102; C12N 15/62; C12N 15/90
See application file for complete search history.

(56) References Cited

U.S. PATENT DOCUMENTS 11,261,435 B2 * 3/2022 Tan .................. C12N 15/11

FOREIGN PATENT DOCUMENTS

| KR | 10-2010-0003223 A | 1/2010 | |
|---|---|---|---|
| KR | 10-2016-0003629 A | 1/2016 | |
| WO | 2017/064566 A2 | 4/2017 | |
| WO | WO 2017/064566 A2 * | 4/2017 | |
| WO | WO-2017064566 A2 * | 4/2017 | ......... A01K 67/0275 |
| WO | 2017/078631 A1 | 5/2017 | |

OTHER PUBLICATIONS

GenBank, "Cloning vector pRH003, complete sequence", KX977486. 1, (Feb. 15, 2017).
Liu et al., "A chemical-inducible CRISPR-Cas9 system for rapid control of genome editing", Nature Chemical Biology, 2016, vol. 12(11), pp. 980-987.

* cited by examiner

*Primary Examiner* — Amy M Bunker
*Assistant Examiner* — Vyoma Shailesh Thakker
(74) *Attorney, Agent, or Firm* — Vorys, Sater Seymour and Pease LLP; Mih Suhn Koh

(57) ABSTRACT

Provided are a protein complex in which estrogen receptor 2 (-ERT2) is fused to CRISPR associated protein 9 (Cas9), and a recombinant vector carrying a gene coding the protein complex, wherein ERT2 is bonded to the N-terminus and C-terminus of nuclear localization sequence (NLS)-removed Cas9 and the complex has the advantage of translocating from the cytosol into the nucleus at a certain time point upon treatment with tamoxifen and modifying a specific DNA with the aid of guide RNA (gRNA), ultimately enabling a more elaborate DNA modification operation in a desired part at a desired time point.

1 Claim, 9 Drawing Sheets
Specification includes a Sequence Listing.

SEQUENCE LISTING

```
<160> NUMBER OF SEQ ID NOS: 15

<210> SEQ ID NO 1
<211> LENGTH: 44
<212> TYPE: DNA
<213> ORGANISM: Artificial Sequence
<220> FEATURE:
<223> OTHER INFORMATION: Forward Primer

<400> SEQUENCE: 1
gacattgatt attgactagt ccttaaagag aggcatccgg ggtc                44

<210> SEQ ID NO 2
<211> LENGTH: 47
<212> TYPE: DNA
<213> ORGANISM: Artificial Sequence
<220> FEATURE:
<223> OTHER INFORMATION: Reverse Primer

<400> SEQUENCE: 2
gttcttctcc tttgctagcc atgacgctca cgctaaagag cttgaag             47

<210> SEQ ID NO 3
<211> LENGTH: 20
<212> TYPE: DNA
<213> ORGANISM: Artificial Sequence
<220> FEATURE:
<223> OTHER INFORMATION: transcriptional intermediary factor 1 gamma
      gRNA 1

<400> SEQUENCE: 3
ggtgcggctg ggcccgacga                                           20
```

-continued

```
<210> SEQ ID NO 4
<211> LENGTH: 20
<212> TYPE: DNA
<213> ORGANISM: Artificial Sequence
<220> FEATURE:
<223> OTHER INFORMATION: transcriptional intermediary factor 1 gamma
      gRNA 2

<400> SEQUENCE: 4
ctacattctt gacgacatac                                                  20

<210> SEQ ID NO 5
<211> LENGTH: 20
<212> TYPE: DNA
<213> ORGANISM: Artificial Sequence
<220> FEATURE:
<223> OTHER INFORMATION: transcriptional intermediary factor 1 gamma
      gRNA 3

<400> SEQUENCE: 5
gaagataatg caagtgcagt                                                  20

<210> SEQ ID NO 6
<211> LENGTH: 21
<212> TYPE: DNA
<213> ORGANISM: Artificial Sequence
<220> FEATURE:
<223> OTHER INFORMATION: Cas9-ERT2 Forward Primer

<400> SEQUENCE: 6
tgctacagaa cagttgcagc c                                                21

<210> SEQ ID NO 7
<211> LENGTH: 21
<212> TYPE: DNA
<213> ORGANISM: Artificial Sequence
<220> FEATURE:
<223> OTHER INFORMATION: Cas9-ERT2 Reverse Primer

<400> SEQUENCE: 7
accttgtact cgtcggtgat c                                                21

<210> SEQ ID NO 8
<211> LENGTH: 27
<212> TYPE: DNA
<213> ORGANISM: Artificial Sequence
<220> FEATURE:
<223> OTHER INFORMATION: transcriptional intermediary factor 1 gamma
      gRNA U6-F

<400> SEQUENCE: 8
gtcgacgagg gcctatttcc catgatt                                          27

<210> SEQ ID NO 9
<211> LENGTH: 20
<212> TYPE: DNA
<213> ORGANISM: Artificial Sequence
<220> FEATURE:
<223> OTHER INFORMATION: transcriptional intermediary factor 1 gamma
      gRNA gRNA1-R

<400> SEQUENCE: 9
tcgtcgggcc cagccgcacc                                                  20

<210> SEQ ID NO 10
<211> LENGTH: 20
<212> TYPE: DNA
```

```
<213> ORGANISM: Artificial Sequence
<220> FEATURE:
<223> OTHER INFORMATION: transcriptional intermediary factor 1 gamma
      gRNA gRNA2-R

<400> SEQUENCE: 10
gtatgtcgtc aagaatgtag                                                20

<210> SEQ ID NO 11
<211> LENGTH: 20
<212> TYPE: DNA
<213> ORGANISM: Artificial Sequence
<220> FEATURE:
<223> OTHER INFORMATION: transcriptional intermediary factor 1 gamma
      gRNA gRNA3-R

<400> SEQUENCE: 11
actgcacttg cattatcttc                                                20

<210> SEQ ID NO 12
<211> LENGTH: 6006
<212> TYPE: DNA
<213> ORGANISM: Artificial Sequence
<220> FEATURE:
<223> OTHER INFORMATION: ERT2-Cas9-ERT2

<400> SEQUENCE: 12
atggctggag acatgagagc tgccaacctt tggccaagcc cgctcatgat caaacgctct      60
aagaagaaca gcctggcctt gtccctgacg gccgaccaga tggtcagtgc cttgttggat     120
gctgagcccc ccatactcta ttccgagtat gatcctacca gacccttcag tgaagcttcg     180
atgatgggct tactgaccaa cctggcagac agggagctgg ttcacatgat caactgggcg     240
aagagggtgc caggctttgt ggatttgacc ctccatgatc aggtccacct tctagaatgt     300
gcctggctag agatcctgat gattggtctc gtctggcgct ccatggagca cccagtgaag     360
ctactgtttg ctcctaactt gctcttggac aggaaccagg gaaaatgtgt agagggcatg     420
gtggagatct tcgacatgct gctggctaca tcatctcggt tccgcatgat gaatctgcag     480
ggagaggagt ttgtgtgcct caaatctatt attttgctta attctggagt gtacacattt     540
ctgtccagca ccctgaagtc tctggaagag aaggaccata tccaccgagt cctggacaag     600
atcacagaca ctttgatcca cctgatggcc aaggcaggcc tgaccctgca gcagcagcac     660
cagcggctgg cccagctcct cctcatcctc tcccacatca ggcacatgag taacaaaggc     720
atggagcatc tgtacagcat gaagtgcaag aacgtggtgc ccctctatga cctgctgctg     780
gaggcggcgg acgcccaccg cctacatgcg cccactagcc gtggagggc atccgtggag      840 gagacggacc aaagccactt ggccactgcg ggctctactt catcgcattc cttgcaaaag     900
tattacatca cggggaggc agagggtttc cctgccacag atctcgacat ggacaagaag     960
tacagcatcg gcctggacat cggcaccaac tctgtgggct gggccgtgat caccgacgag    1020
tacaaggtgc ccagcaagaa attcaaggtg ctgggcaaca ccgaccggca cagcatcaag    1080
aagaacctga tcggagccct gctgttcgac agcggcgaaa cagccgaggc cacccggctg    1140
aagagaaccg ccagaagaag ataccaccaga cggaagaacc ggatctgcta tctgcaagag    1200
atcttcagca acgagatggc caaggtggac gacagcttct ccacagact ggaagagtcc    1260 ttcctggtgg aagaggataa gaagcacgag cggcacccca tcttcggcaa catcgtggac    1320
gaggtggcct accacgagaa gtaccccacc atctaccacc tgagaaagaa actggtggac    1380
agcaccgaca aggccgacct gcggctgatc tatctggccc tggcccacat gatcaagttc    1440
```

```
cggggccact tcctgatcga gggcgacctg aaccccgaca acagcgacgt ggacaagctg   1500
ttcatccagc tggtgcagac ctacaaccag ctgttcgagg aaaacccat caacgccagc   1560 ggcgtggacg ccaaggccat cctgtctgcc agactgagca agagcagacg gctggaaaat   1620
ctgatcgccc agctgcccgg cgagaagaag aatggcctgt tcggaaacct gattgccctg   1680
agcctgggcc tgaccccaa cttcaagagc aacttcgacc tggccgagga tgccaaactg   1740
cagctgagca aggacaccta cgacgacgac ctggacaacc tgctggccca gatcggcgac   1800
cagtacgccg acctgtttct ggccgccaag aacctgtccg acgccatcct gctgagcgac   1860
atcctgagag tgaacaccga gatcaccaag gcccccctga cgcctctat gatcaagaga   1920 tacgacgagc accaccagga cctgaccctg ctgaaagctc tcgtgcggca gcagctgcct   1980
gagaagtaca agagattttt cttcgaccag agcaagaacg gctacgccgg ctacattgac   2040
ggcggagcca gccaggaaga gttctacaag ttcatcaagc ccatcctgga aaagatggac   2100
ggcaccgagg aactgctcgt gaagctgaac agagaggacc tgctgcggaa gcagcggacc   2160
ttcgacaacg gcagcatccc ccaccagatc cacctgggag agctgcacgc cattctgcgg   2220
cggcaggaag attttttaccc attcctgaag gacaaccggg aaaagatcga agatcctg   2280 accttccgca tccctacta cgtgggccct ctggccaggg aaacagcag attcgcctgg   2340 atgaccagaa agagcgagga aaccatcacc ccctggaact tcgaggaagt ggtggacaag   2400
ggcgcttccg cccagagctt catcgagcgg atgaccaact tcgataagaa cctgcccaac   2460
gagaaggtgc tgcccaagca cagcctgctg tacgagtact tcaccgtgta taacgagctg   2520
accaaagtga aatacgtgac cgagggaatg agaaagcccg ccttcctgag cggcgagcag   2580
aaaaaggcca tcgtggacct gctgttcaag accaaccgga aagtgaccgt gaagcagctg   2640
aaagaggact acttcaagaa aatcgagtgc ttcgactccg tggaaatctc cggcgtggaa   2700
gatcggttca acgcctccct gggcacatac cacgatctgc tgaaaattat caaggacaag   2760
gacttcctgg acaatgagga aaacgaggac attctggaag atatcgtgct gaccctgaca   2820
ctgtttgagg acagagagat gatcgaggaa cggctgaaaa cctatgccca cctgttcgac   2880
gacaaagtga tgaagcagct gaagcggcgg agatacaccg ctgggggcag gctgagccgg   2940
aagctgatca acggcatccg ggacaagcag tccggcaaga caatcctgga tttcctgaag   3000
tccgacggct cgccaacag aaacttcatg cagctgatcc acgacgacag cctgaccttt   3060
aaagaggaca tccagaaagc ccaggtgtcc ggccagggcg atagcctgca cgagcacatt   3120
gccaatctgg ccggcagccc cgccattaag aagggcatcc tgcagacagt gaaggtggtg   3180
gacgagctcg tgaaagtgat gggccggcac aagcccgaga acatcgtgat cgaaatggcc   3240
agagagaacc agaccaccca gaagggacag aagaacagcc gcgagagaat gaagcggatc   3300
gaagagggca tcaaagagct gggcagccag atcctgaaag aacacccgt ggaaaacacc   3360 cagctgcaga acgagaagct gtacctgtac tacctgcaga atgggcggga tatgtacgtg   3420
gaccaggaac tggacatcaa ccggctgtcc gactacgatg tggaccatat cgtgcctcag   3480
agctttctga aggacgactc catcgacaac aaggtgctga ccagaagcga caagaaccgg   3540
ggcaagagcg acaacgtgcc ctccgaagag gtcgtgaaga gatgaagaa ctactggcgg   3600 cagctgctga acgccaagct gattacccag agaaagttcg acaatctgac caaggccgag   3660
agaggcggcc tgagcgaact ggataaggcc ggcttcatca agagacagct ggtggaaacc   3720
cggcagatca caaagcacgt ggcacagatc ctggactccc ggatgaacac taagtacgac   3780
```

-continued

```
gagaatgaca agctgatccg ggaagtgaaa gtgatcaccc tgaagtccaa gctggtgtcc    3840
gatttccgga aggatttcca gttttacaaa gtgcgcgaga tcaacaacta ccaccacgcc    3900
cacgacgcct acctgaacgc cgtcgtggga accgccctga tcaaaaagta ccctaagctg    3960
gaaagcgagt tcgtgtacgg cgactacaag gtgtacgacg tgcggaagat gatcgccaag    4020
agcgagcagg aaatcggcaa ggctaccgcc aagtacttct tctacagcaa catcatgaac    4080
tttttcaaga ccgagattac cctggccaac ggcgagatcc ggaagcggcc tctgatcgag    4140
acaaacggcg aaaccgggga gatcgtgtgg gataagggcc gggattttgc caccgtgcgg    4200
aaagtgctga gcatgcccca agtgaatatc gtgaaaaaga ccgaggtgca gacaggcggc    4260
ttcagcaaag agtctatcct gcccaagagg aacagcgata gctgatcgc cagaaagaag    4320 gactgggacc ctaagaagta cggcggcttc gacagcccca ccgtggccta ttctgtgctg    4380
gtggtggcca aagtggaaaa gggcaagtcc aagaaactga gagtgtgaa agagctgctg    4440 gggatcacca tcatggaaag aagcagcttc gagaagaatc ccatcgactt tctggaagcc    4500
aagggctaca agaagtgaa aaaggacctg atcatcaagc tgcctaagta ctccctgttc    4560
gagctggaaa acggccggaa gagaatgctg gcctctgccg gcgaactgca gaagggaaac    4620
gaactggccc tgcccctcaa atatgtgaac ttcctgtacc tggccagcca ctatgagaag    4680
ctgaagggct cccccgagga taatgagcag aaacagctgt tgtggaaca gcacaagcac    4740 tacctggacg agatcatcga gcagatcagc gagttctcca agagagtgat cctggccgac    4800
gctaatctgg acaaagtgct gtccgcctac aacaagcacc gggataagcc catcagagag    4860
caggccgaga atatcatcca cctgtttacc ctgaccaatc tgggagcccc tgccgccttc    4920
aagtactttg acaccaccat cgaccggaag aggtacacca gcaccaaaga ggtgctggac    4980
gccaccctga tccaccagag catcaccggc ctgtacgaga cacggatcga cctgagccag    5040
ctgggcggcg acctcgagcc atctgctgga gacatgagag ctgccaacct ttggccaagc    5100
ccgctcatga tcaaacgctc taagaagaac agcctggcct tgtccctgac ggccgaccag    5160
atggtcagtg ccttgttgga tgctgagccc cccatactct attccgagta tgatcctacc    5220
agacccttca gtgaagcttc gatgatgggc ttactgacca acctggcaga cagggagctg    5280
gttcacatga tcaactgggc gaagagggtg ccaggctttg tggatttgac cctccatgat    5340
caggtccacc ttctagaatg tgcctggcta gagatcctga tgattggtct cgtctggcgc    5400
tccatggagc acccagtgaa gctactgttt gctcctaact tgctcttgga caggaaccag    5460
ggaaaatgtg tagagggcat ggtggagatc ttcgacatgc tgctggctac atcatctcgg    5520
ttccgcatga tgaatctgca gggagaggag tttgtgtgcc tcaaatctat tattttgctt    5580
aattctggag tgtacacatt tctgtccagc accctgaagt ctctggaaga aaggaccat    5640 atccaccgag tcctggacaa gatcacagac actttgatcc acctgatggc caaggcaggc    5700
ctgaccctgc agcagcagca ccagcggctg gcccagctcc tctcatcct ctcccacatc    5760 aggcacatga gtaacaaagg catggagcat ctgtacagca tgaagtgcaa gaacgtggtg    5820
cccctctatg acctgctgct ggaggcggcg gacgcccacc gcctacatgc gcccactagc    5880
cgtggagggg catccgtgga ggagacggac caaaagccact tggccactgc gggctctact    5940
tcatcgcatt ccttgcaaaa gtattacatc acggggggag cagagggttt ccctgccaca    6000
gcttga                                                               6006
```

<210> SEQ ID NO 13
<211> LENGTH: 241

```
<212> TYPE: DNA
<213> ORGANISM: Artificial Sequence
<220> FEATURE:
<223> OTHER INFORMATION: RNA polymerase III promoter for human U6 snRNA

<400> SEQUENCE: 13
gtcctttcca caagatatat aaagccaaga atcgaaata ctttcaagtt acggtaagca    60
tatgatagtc cattttaaaa cataatttta aaactgcaaa ctacccaaga aattattact   120
ttctacgtca cgtattttgt actaatatct ttgtgtttac agtcaaatta attccaatta   180
tctctctaac agccttgtat cgtatatgca aatatgaagg aatcatggga aataggccct   240
c                                                                   241

<210> SEQ ID NO 14
<211> LENGTH: 204
<212> TYPE: DNA
<213> ORGANISM: Artificial Sequence
<220> FEATURE:
<223> OTHER INFORMATION: human cytomegalovirus (CMV) immediate early
      promoter

<400> SEQUENCE: 14
gtgatgcggt tttggcagta catcaatggg cgtggatagc ggtttgactc acggggattt    60
ccaagtctcc accccattga cgtcaatggg agtttgtttt ggcaccaaaa tcaacgggac   120
tttccaaaat gtcgtaacaa ctccgcccca ttgacgcaaa tgggcggtag cgtgtacgg   180 tgggaggtct atataagcag agct                                          204

<210> SEQ ID NO 15
<211> LENGTH: 4104
<212> TYPE: DNA
<213> ORGANISM: Artificial Sequence
<220> FEATURE:
<223> OTHER INFORMATION: Cas9 (Csn1) endonuclease from the Streptococcus
      pyogenes Type II CRISPR/Cas system

<400> SEQUENCE: 15
atggacaaga agtacagcat cggcctggac atcggcacca actctgtggg ctgggccgtg    60
atcaccgacg agtacaaggt gcccagcaag aaattcaagg tgctgggcaa caccgaccgg   120
cacagcatca agaagaacct gatcggagcc ctgctgttcg acagcggcga aacagccgag   180
gccacccggc tgaagagaac cgccagaaga agatacacca gacggaagaa ccggatctgc   240
tatctgcaag agatcttcag caacgagatg gccaaggtgg acgacagctt cttccacaga   300
ctggaagagt cctttcctgg tggaagaggat aagaagcacg agcggcaccc catcttcggc   360
aacatcgtgg acgaggtggc ctaccacgag aagtacccca ccatctacca cctgagaaag   420
aaactggtgg acagcaccga caaggccgac ctgcggctga tctatctggc cctggcccac   480
atgatcaagt tccggggcca cttcctgatc gagggcgacc tgaaccccga caacagcgac   540
gtggacaagc tgttcatcca gctggtgcag acctacaacc agctgttcga ggaaaacccc   600
atcaacgcca gcggcgtgga cgccaaggcc atcctgtctg ccagactgag caagagcaga   660
cggctggaaa atctgatcgc ccagctgccc ggcgagaaga gaatggcct gttcggaaac   720 ctgattgccc tgagcctggg cctgaccccc aacttcaaga gcaacttcga cctggccgag   780
gatgccaaac tgcagctgag caaggacacc tacgacgacg acctggacaa cctgctggcc   840
cagatcggcg accagtacgc cgacctgttt ctggccgcca gaaacctgtc cgacgccatc   900
ctgctgagcg acatcctgag agtgaacacc gagatcacca aggccccccct gagcgcctct   960
```

-continued

```
atgatcaaga gatacgacga gcaccaccag gacctgaccc tgctgaaagc tctcgtgcgg   1020
cagcagctgc ctgagaagta caaagagatt ttcttcgacc agagcaagaa cggctacgcc   1080
ggctacattg acggcggagc cagccaggaa gagttctaca agttcatcaa gcccatcctg   1140
gaaaagatgg acggcaccga ggaactgctc gtgaagctga acagagagga cctgctgcgg   1200
aagcagcgga ccttcgacaa cggcagcatc ccccaccaga tccacctggg agagctgcac   1260
gccattctgc ggcggcagga agattttttac ccattcctga aggacaaccg ggaaaagatc   1320
gagaagatcc tgaccttccg catcccctac tacgtgggcc ctctggccag ggaaacagc    1380 agattcgcct ggatgaccag aaagagcgag gaaaccatca ccccctgaa cttcgaggaa    1440 gtggtggaca agggcgcttc cgcccagagc ttcatcgagc ggatgaccaa cttcgataag   1500
aacctgccca cgagaaggt gctgcccaag cacagcctgc tgtacgagta cttcaccgtg    1560
tataacgagc tgaccaaagt gaaatacgtg accgagggaa tgagaaagcc cgccttcctg   1620
agcggcgagc agaaaaaggc catcgtggac ctgctgttca agaccaaccg gaaagtgacc   1680
gtgaagcagc tgaaagagga ctacttcaag aaaatcgagt gcttcgactc cgtggaaatc   1740
tccggcgtgg aagatcggtt caacgcctcc ctgggcacat accacgatct gctgaaaatt   1800
atcaaggaca aggacttcct ggacaatgag gaaaacgagg acattctgga agatatcgtg   1860
ctgaccctga cactgtttga ggacagagag atgatcgagg aacggctgaa aacctatgcc   1920
cacctgttcg acgacaaagt gatgaagcag ctgaagcggc ggagatacac cggctggggc   1980
aggctgagcc ggaagctgat caacggcatc cgggacaagc agtccggcaa gacaatcctg   2040
gatttcctga agtccgacgg cttcgccaac agaaacttca tgcagctgat ccacgacgac   2100
agcctgacct ttaaagagga catccagaaa gcccaggtgt ccggccaggg cgatagcctg   2160
cacgagcaca ttgccaatct ggccggcagc cccgccatta agaagggcat cctgcagaca   2220
gtgaaggtgg tggacgagct cgtgaaagtg atgggccggc acaagcccga aacatcgtg    2280 atcgaaatgg ccagagagaa ccagaccacc agaagggac agaagaacag ccgcgagaga    2340
atgaagcgga tcgaagaggg catcaaagag ctgggcagcc agatcctgaa agaacacccc   2400
gtggaaaaca cccagctgca gaacgagaag ctgtacctgt actacctgca gaatgggcgg   2460
gatatgtacg tggaccagga actggacatc aaccggctgt ccgactacga tgtggaccat   2520
atcgtgcctc agagctttct gaaggacgac tccatcgaca caaggtgct gaccagaagc    2580 gacaagaacc ggggcaagag cgacaacgtg ccctccgaag aggtcgtgaa aagatgaag    2640 aactactggc ggcagctgct gaacgccaag ctgattaccc agagaaagtt cgacaatctg   2700
accaaggccg agagaggcgg cctgagcgaa ctggataagg ccggcttcat caagagacag   2760
ctggtggaaa cccggcagat cacaaagcac gtggcacaga tcctggactc ccggatgaac   2820
actaagtacg acgagaatga caagctgatc cgggaagtga aagtgatcac cctgaagtcc   2880
aagctggtgt ccgatttccg gaaggatttc cagtttttaca agtgcgcga gatcaacaac   2940 taccaccacg cccacgacgc ctacctgaac gccgtcgtgg aaccgccct gatcaaaaag    3000 taccctaagc tggaaagcga gttcgtgtac ggcgactaca aggtgtacga cgtgcggaag   3060
atgatcgcca gagcgagca ggaaatcggc aaggctaccg ccaagtactt cttctacagc    3120
aacatcatga actttttcaa gaccgagatt accctggcca acgcgagat ccggaagcgg    3180 cctctgatcg agacaaacgg cgaaaccggg gagatcgtgt gggataaggg ccgggatttt   3240
gccaccgtgc ggaaagtgct gagcatgccc caagtgaata tcgtgaaaaa gaccgaggtg   3300
cagacaggcg gcttcagcaa agagtctatc ctgcccaaga ggaacagcga taagctgatc   3360
```

-continued

```
gccagaaaga aggactggga ccctaagaag tacggcggct tcgacagccc caccgtggcc    3420
tattctgtgc tggtggtggc caaagtggaa aagggcaagt ccaagaaact gaagagtgtg    3480
aaagagctgc tggggatcac catcatggaa agaagcagct tcgagaagaa tcccatcgac    3540
tttctggaag ccaagggcta caagaagtg aaaaaggacc tgatcatcaa gctgcctaag    3600
tactccctgt tcgagctgga aaacggccgg aagagaatgc tggcctctgc cggcgaactg    3660
cagaagggaa acgaactggc cctgccctcc aaatatgtga acttcctgta cctggccagc    3720
cactatgaga agctgaaggg ctcccccgag gataatgagc agaaacagct gtttgtggaa    3780
cagcacaagc actacctgga cgagatcatc gagcagatca gcgagttctc caagagagtg    3840
atcctggccg acgctaatct ggacaaagtg ctgtccgcct acaacaagca ccgggataag    3900
cccatcagag agcaggccga gaatatcatc cacctgttta ccctgaccaa tctgggagcc    3960
cctgccgcct tcaagtactt tgacaccacc atcgaccgga gaggtacac cagcaccaaa    4020 gaggtgctgg acgccaccct gatccaccag agcatcaccg gcctgtacga gacacggatc    4080
gacctgagcc agctgggcgg cgac                                          4104
```

RECOMBINANT VECTOR COMPRISING ERT2 FUSED TO CAS9

CROSS-REFERENCE TO RELATED APPLICATIONS

This application is a 371 of PCT/KR2018/005135, filed May 3, 2018, which claims the benefit of priority from Korean Patent Application No. 10-2017-0077221, filed Jun. 19, 2017, the contents of each of which are incorporated herein by reference in its entirety.

SEQUENCE LISTING

The Sequence Listing submitted in text format (.txt) filed on Dec. 19, 2019, named "SequenceListing.txt", created on Dec. 10, 2019 (15.9 KB), is incorporated herein by reference.

TECHNICAL FIELD

The present invention relates to a DNA modification-inducing protein complex and a recombinant vector comprising a gene encoding the same.

BACKGROUND ART

To modify target DNA in a desired region at specific time, a method using tissue-specific promoters in Cre-Lox recombination, a TET system, and the like is currently used.

Among these, the TET system refers to a system for inducing gene expression in mammalian culture cells and animal individuals by using a tetracycline (Tc) resistance expression control system present in transposon Tn10 of *Escherichia coli*, and consists of two elements. The first element is a tetracyclin-controlled transactivator (tTA), which is a protein obtained by binding the transcriptional activation region, which is herpes simplex virus VP16, to a Tc inhibitor (tetR), and the second element is placement of a target gene downstream of an operator (tetO) capable of binding to tetR and a human cytomegalovirus (CMV) promoter. In the presence of Tc, tTA bound thereto is unable to bind to tetO, but when Tc is removed, tTA binds to tetO to induce the expression of a target gene (TET-OFF system). Conversely, research for the construction of a TET-ON system using a reverse tetracyclin-controlled transactivator (rtTA), which induces the expression of a target gene by binding to tetO, is ongoing.

Cre-Lox recombination is a site-specific recombinase technique used to perform deletion, insertion, translocation, and inversion at specific sites of cellular DNA, and runs in both eukaryotic and prokaryotic systems, allowing DNA modification to target specific cell types or to be triggered by specific external stimuli. In particular, Cre-lox recombination systems are useful for neurologists to study the brain where complex cell types and neural circuits come together to generate cognition and behavior.

However, the above-described DNA modification methods are limited in that the procedures are complicated and take a lot of time, and when drug treatment is performed to modify DNA at a desired site in an animal model produced therethrough, precise work is not performed, and thus there are many cases where the results are not reliable, and therefore, significant studies on DNA modification such as DNA modification by single molecule manipulation (Korean Patent Publication No. 10-2016-0003629) have been continuously conducted.

Meanwhile, among various DNA modification methods, a Cas9 system enables an animal model to be produced at low cost within a relatively short period of time and facilitates precise work on DNA, but research thereon is still inadequate despite the fact that a method for inducing DNA modification at a specific time and a desired site is necessary.

DESCRIPTION OF EMBODIMENTS

Technical Problem

To address the above-described conventional problems, as a result of having conducted intensive studies on a method capable of inducing DNA modification at a desired time and desired specific region by using Cas9, the inventors of the present invention confirmed that, by treating a Cas9-ERT2 protein complex with tamoxifen, the Cas9-ERT2 could be transported from the cytoplasm into the nucleus at a specific time, and the Cas9-ERT2 protein complex transported into the nucleus was able to modify specific DNA through guide RNA, and thus completed the present invention based on these findings.

Therefore, the present invention relates to a protein complex in which estrogen receptor 2 is fused to CRISPR associated protein 9 (Cas9), and more particularly an object of the present invention is to provide a protein complex in which the ERT2 is bound to the N-terminus and C-terminus of Cas9 from which a nuclear localization sequence (NLS) is removed.

Another object of the present invention is to provide a recombinant vector comprising a gene encoding the protein complex, wherein the gene consists of the nucleotide sequence of SEQ ID NO: 12.

Still another object of the present invention is to provide a transgenic animal produced by implanting an embryo, with the recombinant vector micro-injected thereinto, into a recipient animal and a method of producing the corresponding transgenic animal.

However, technical problems to be solved by the present invention are not limited to the above-described technical problems, and other unmentioned technical problems will become apparent from the following description to those of ordinary skill in the art.

Technical Solution

According to an aspect of the present disclosure, there is provided a protein complex in which estrogen receptor 2 (ERT2) is fused to CRISPR associated protein 9 (Cas9), wherein the ERT2 is bound to the N-terminus and C-terminus of Cas9 from which a nuclear localization sequence (NLS) is removed.

In one embodiment of the present invention, the protein complex is transported from the cytoplasm into the nucleus by tamoxifen treatment, but the present invention is not limited thereto.

The present invention also provides a recombinant vector comprising a gene encoding the protein complex, wherein the gene consists of the nucleotide sequence of SEQ ID NO: 12.

In one embodiment of the present invention, the recombinant vector may further include guide RNA (gRNA) and a promoter.

In another embodiment of the present invention, the promoter may be a cytomegalovirus (CMV) promoter, but the present invention is not limited thereto.

The present invention also provides a transgenic animal produced by implanting an embryo with the recombinant vector micro-injected thereinto, into a recipient animal.

In one embodiment of the present invention, the transgenic animal may be a mouse, but the present invention is not limited thereto.

The present invention also provides a method of producing a transgenic animal, including: a) constructing a recombinant vector according to the present invention; b) microinjecting the recombinant vector into an embryo; and c) implanting the embryo into the fallopian tube of a recipient animal by using a surgical method.

In one embodiment of the present invention, the recombinant vector of process a) may further include gRNA and a promoter.

In another embodiment of the present invention, the recipient animal may be a mouse, but the present invention is not limited thereto.

Advantageous Effects of Invention

A protein complex according to the present invention, in which ERT2 is bound to the N-terminus and C-terminus of Cas9 from which a nuclear localization sequence (NLS) is removed, is advantageous in that the protein complex is able to be transported from the cytoplasm into the nucleus at a desired specific time by tamoxifen treatment. The protein complex transported into the nucleus can modify specific DNA through guide RNA (gRNA), enabling more precise DNA modification work at a desired time and a desired site, and thus the present invention is expected to be applied to develop a new and convenient DNA modification technique.

BEST MODE

Figure 1:
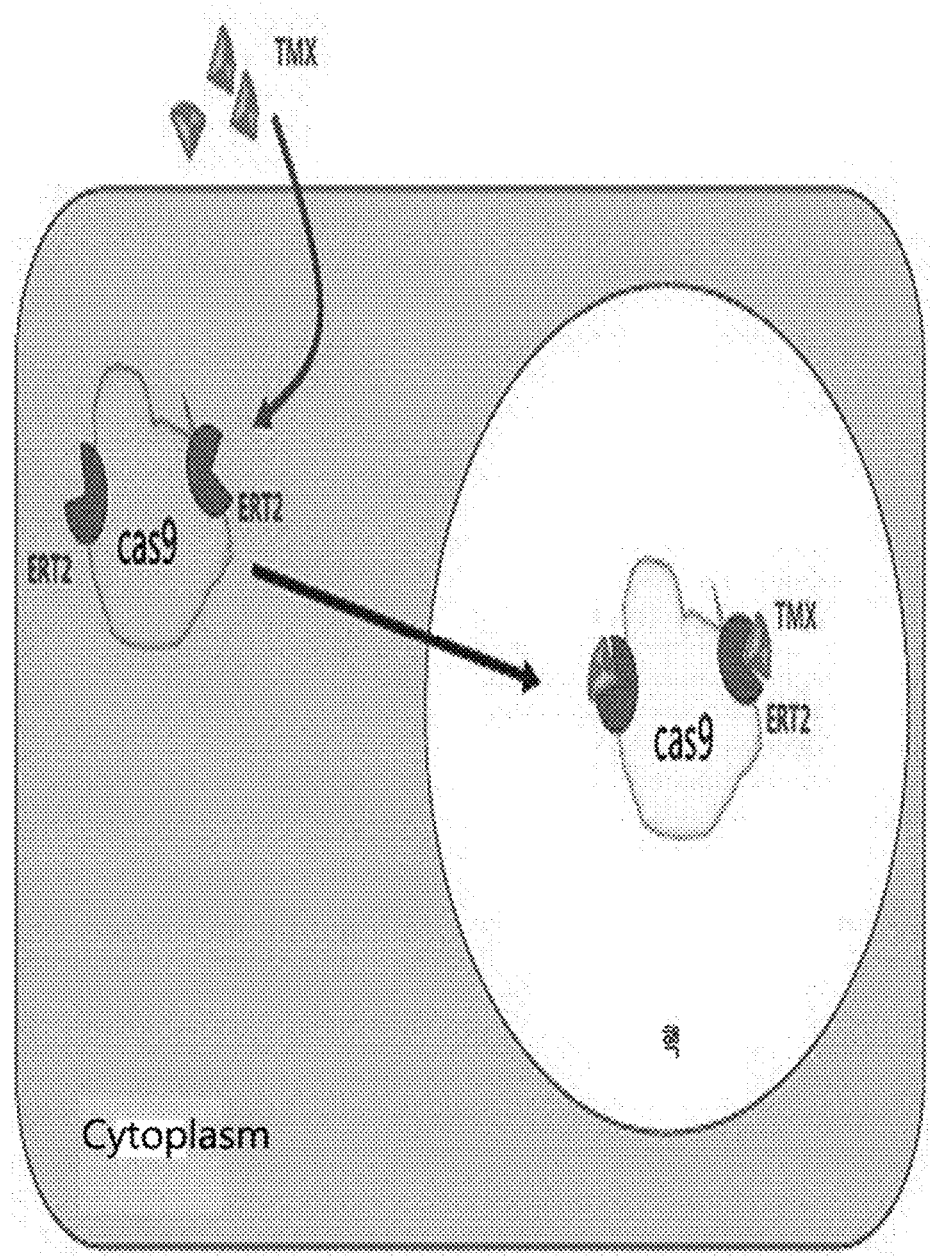
FIG. 1 is a view illustrating a process for the transport of a Cas9-ERT2 protein complex, which is present in the cytoplasm, into the nucleus by tamoxifen (TMX) treatment.

The inventors of the present invention confirmed that, by treating a Cas9-ERT2 protein complex with tamoxifen, the Cas9-ERT2 could be transported from the cytoplasm into the nucleus at a specific time, and the Cas9-ERT2 protein complex transported into the nucleus was able to modify specific DNA by recognizing guide RNA, and thus completed the present invention based on these findings.

Hereinafter, the present invention will be described in detail.

The present invention provides a protein complex in which estrogen receptor 2 (ERT2) is fused to CRISPR associated protein 9 (Cas9), wherein the ERT2 is bound to the N-terminus and C-terminus of Cas9 from which a nuclear localization sequence (NLS) is removed.

In the present invention, "Cas9", which is an abbreviation of "CRISPR associated protein 9", refers to "CRISPR-CAS9", and CRISPR-CAS9 is a third generation gene scissors, which recognizes a specific nucleotide sequence to be used and cleaves and edits the sequence, and is useful for simple, rapid, and efficient manipulation of inserting a specific gene into a target location of a genome or stopping the activity of a specific gene.

In the present invention, "ERT2", which is an abbreviation of "Estrogen receptor 2", refers to an estrogen receptor, and the estrogen receptor acts as a transcriptional regulator that promotes hormone-dependent transcription by binding, as a homodimer, to an estrogen-responsive amplicon sequence present in target gene promoters (common sequence: 5'-AGGTCANNNTGACCT-3').

In the present invention, "gRNA" is an abbreviation of "guide RNA" and refers to a small RNA of 45 to 70 nucleotides that has nucleotide sequence information, which is a template for a modification reaction when editing RNA, in which the 5'-side region of gRNA is in an order complementary to a portion of mRNA that is RNA-edited, enabling gRNA to bind to mRNA via this region, a nucleotide sequence complementary to the order of the final mRNA after editing is present in the 3'-side region of gRNA, and RNA modification, such as the insertion or deletion of uridine, occurs according to the sequence information.

The present invention also provides a recombinant vector including a gene encoding the protein complex, wherein the gene consisting of the nucleotide sequence of SEQ ID NO: 12.

In the present invention, "vector" refers to DNA used in a DNA recombination experiment, which enables the introduction of a target DNA fragment into a host bacterium or the like and proliferation thereof, and is also referred to as a cloning vehicle, and vector DNA is cleaved and opened by an restriction enzyme or the like, and a target DNA fragment is inserted thereinto and linked thereto, followed by introduction into a host bacterium. The vector DNA to which the target DNA fragment is linked replicates as the host bacterium proliferates and is distributed to each daughter cell as well as the division of the bacterium, thereby maintaining the target DNA fragment from generation to generation, and plasmids and phage chromosomes are mainly used.

The present invention also provides a transgenic animal produced by implanting, into a recipient animal, an embryo into which a recombinant vector constructed according to the present invention is microinjected.

Another embodiment of the present invention provides a method of producing a transgenic animal, including: a) constructing a recombinant vector according to the present invention; b) microinjecting the recombinant vector into an embryo; and c) implanting the embryo into the fallopian tube of a recipient animal by using a surgical method.

In one embodiment of the present invention, to produce a protein complex capable of inducing DNA modification at a desired time and a specific site by using Cas9, a structure for linking Cas9 and ERT2 was designed (see Example 1).

In another embodiment of the present invention, a recombinant vector including a gene encoding the protein complex was constructed (see Example 2). An embryo with the recombinant vector microinjected thereinto was generated to produce transgenic mice (see Example 3).

In another embodiment of the present invention, immunostaining was performed to confirm an expression pattern of the protein complex (see Example 4).

Hereinafter, exemplary examples will be described to aid in understanding of the present invention. However, the following examples are provided only to facilitate the understanding of the present invention and are not intended to limit the scope of the present invention.

MODE OF INVENTION

Example 1. Preparation of DNA Modification-Inducing Protein Complex

Figure 2A:
FIG. 2a illustrates the structure of a Cas9-ERT2 protein complex in which ERT2 is fused to the N-terminus and C-terminus of Cas9 from which a nuclear localization signal (NLS) is removed.

To prepare a DNA modification-inducing protein complex, as illustrated in FIG. 1, to more precisely regulate Cas9 which is transported into the nucleus upon expression, the inventors of the present invention allowed Cas9 to be present in the cytoplasm by removing a nuclear localization signal (NLS) therefrom, and designed the structure of a Cas9-ERT2 protein complex (ERT2-Cas9-ERT2) capable of being transported into the nucleus at a specific time by treating tamoxifen (TMX), a Cas9-ERT2 protein complex prepared by fusing ERT2 to the N-terminus and C-terminus of Cas9 from which the NLS was removed (see FIG. 2a).

Figure 2B:
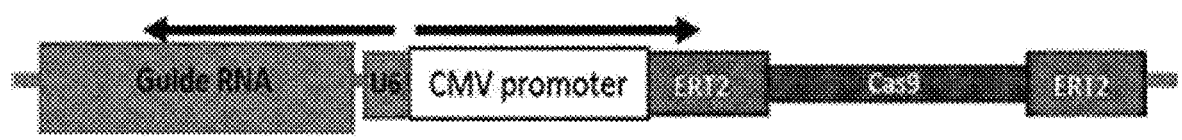
FIG. 2b illustrates the structure in which guide RNA (gRNA) of a specific gene to be inhibited, a U6 promoter, a cytomegalovirus (CMV) promoter, and Cas9-ERT2 are linked to one another.
Figure 3:
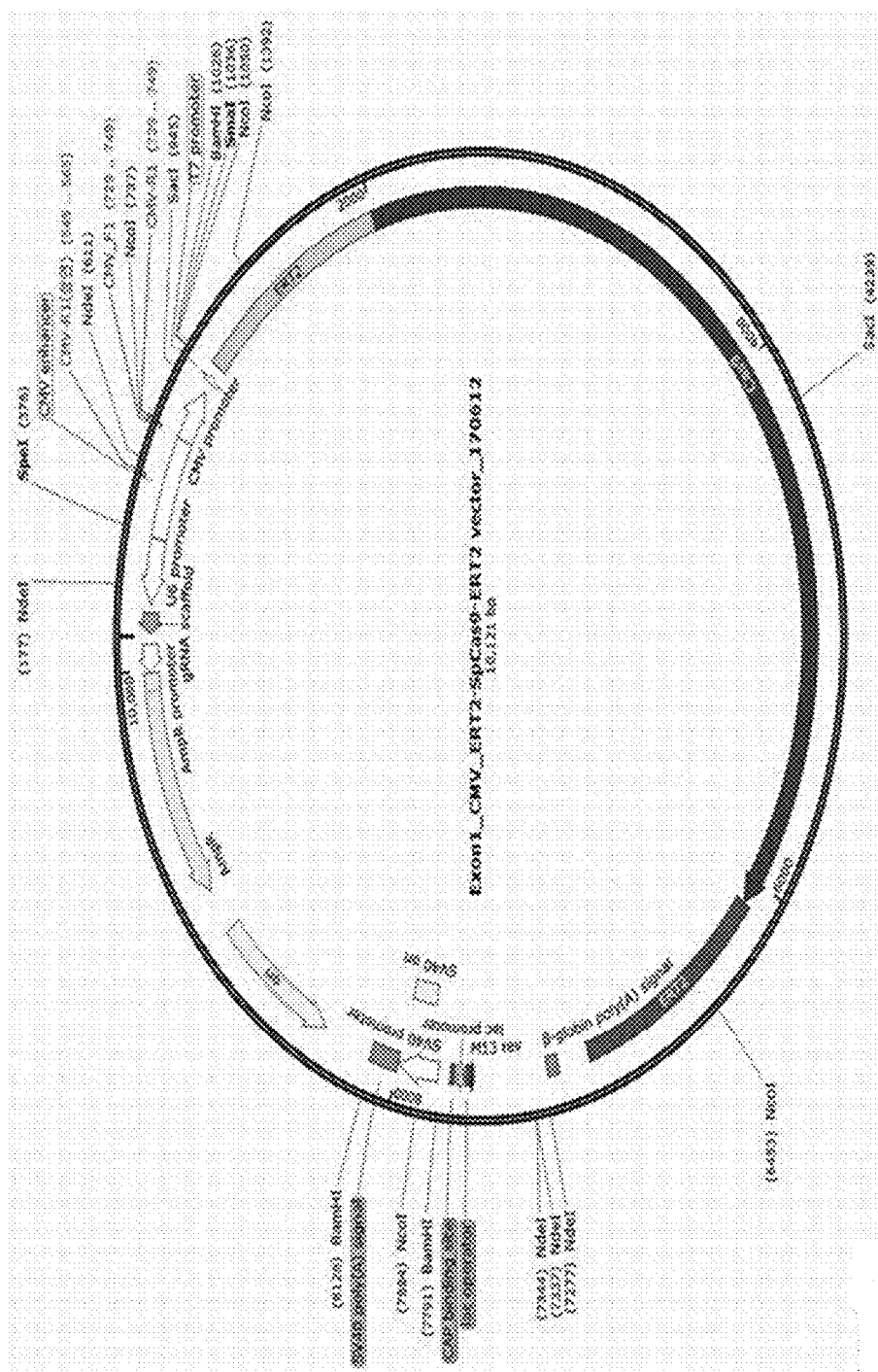
FIG. 3 illustrates the map of a recombinant vector including a gene encoding a protein complex according to an embodiment of the present invention.

Specifically, to modify a specific gene at a desired time, the inventors designed a structure in which guide RNA (gRNA) of a specific gene, a U6 promoter, a CMV promoter, and the Cas9-ERT2 protein complex were linked to each other (see FIG. 2b). At this time, ubiquitous expression is possible due to the use of the CMV promoter.

Example 2. Construction of Recombinant Vector

Figure 4:
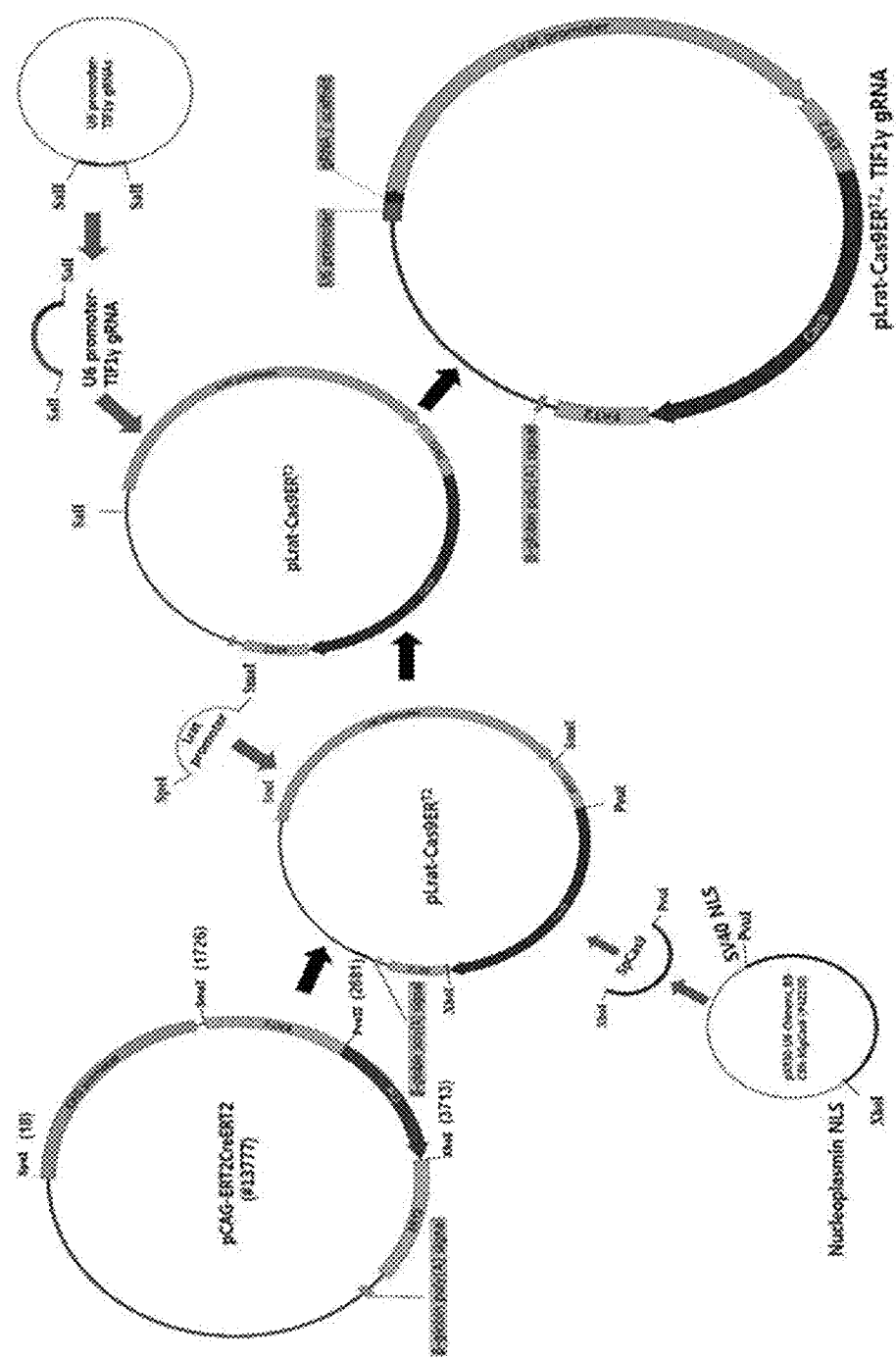
FIG. 4 schematically illustrates a process for constructing a recombinant vector according to an embodiment of the present invention.

In one embodiment of the present invention, a recombinant vector including a gene encoding the protein complex of the present invention was constructed (see FIG. 4). Specifically, pCAG-ERT2CreERT2 (#13777) and pX330-U6-Chimeric_BB-CBh-hSpCas9 (#42230) plasmids were purchased from Addgene, and a mouse TIF1γ CRISPR/Cas9 knockout (KO) plasmid (sc-430111) was purchased from Santa Cruz. For the mouse lecithin retinol acyltransferase (LRAT) promoter sequence, sequences (−5,500 to +72 bps) expected to have high activity were selected using promoter prediction (http://gpminer dot mbcc dot nctu dot edu dot tw/index dot php, and PCR was carried out using specific primers shown in Table 1 below using normal mouse DNA (C57BL/6N) to obtain a LRAT promoter.

TABLE 1

| Primer sequence (5'-3') | |
|---|---|
| Forward | GACTTGATTATTGACTAGTCCTTAAAGAGAGGCATCCGGGGTC |
| Reverse | GTTCTTCTCCTTTGCTAGCCATGACGCTCACGCTAAAGAGCTTGAAG |

To produce a plasmid which is dependent on the LRAT promoter and in which the regulation of liver fibrosis inhibitory gene (TIF1γ) expression is induced by tamoxifen, a CAG promoter and Cre of pCAG-ERT2CreERT2 were replaced with the LRAT promoter and *Streptococcus pyogenes* Cas9 (SpCas9), respectively.

Next, TIF1γ gRNAs shown in Table 2 below having a U6 promoter were inserted into the plasmid, respectively.

TABLE 2

| gRNA sequence (5'-3') | |
|---|---|
| gRNA 1 | GGTGCGGCTGGGCCCGACGA |
| gRNA 2 | CTACATTCTTGACGACATAC |
| gRNA 3 | GAAGATAATGCAAGTGCAGT |

The prepared pLrat-ERT2Cas9ERT2-TIF1γ gRNA plasmid was identified by Sanger sequencing.

Example 3. Production of Transgenic Mice

To produce transgenic (TG) mice in which specific gene expression is regulated by tamoxifen at a specific time, pregnant mare serum gonadotrophin (PMSG) (7.5 IU) and human chorionic gonadotropin (hCG) (5 IU) were intraperitoneally (IP) injected into 5- to 8-week-old C57BL/6N female mice at intervals of 48 hours each to induce superovulation, and after hCG injection, the female mice were crossed with C57BL/6N male mice. Virginal plugs were used to determine whether the female mice were pregnant, and fertilized embryos were harvested from the female mice.

Figure 5:
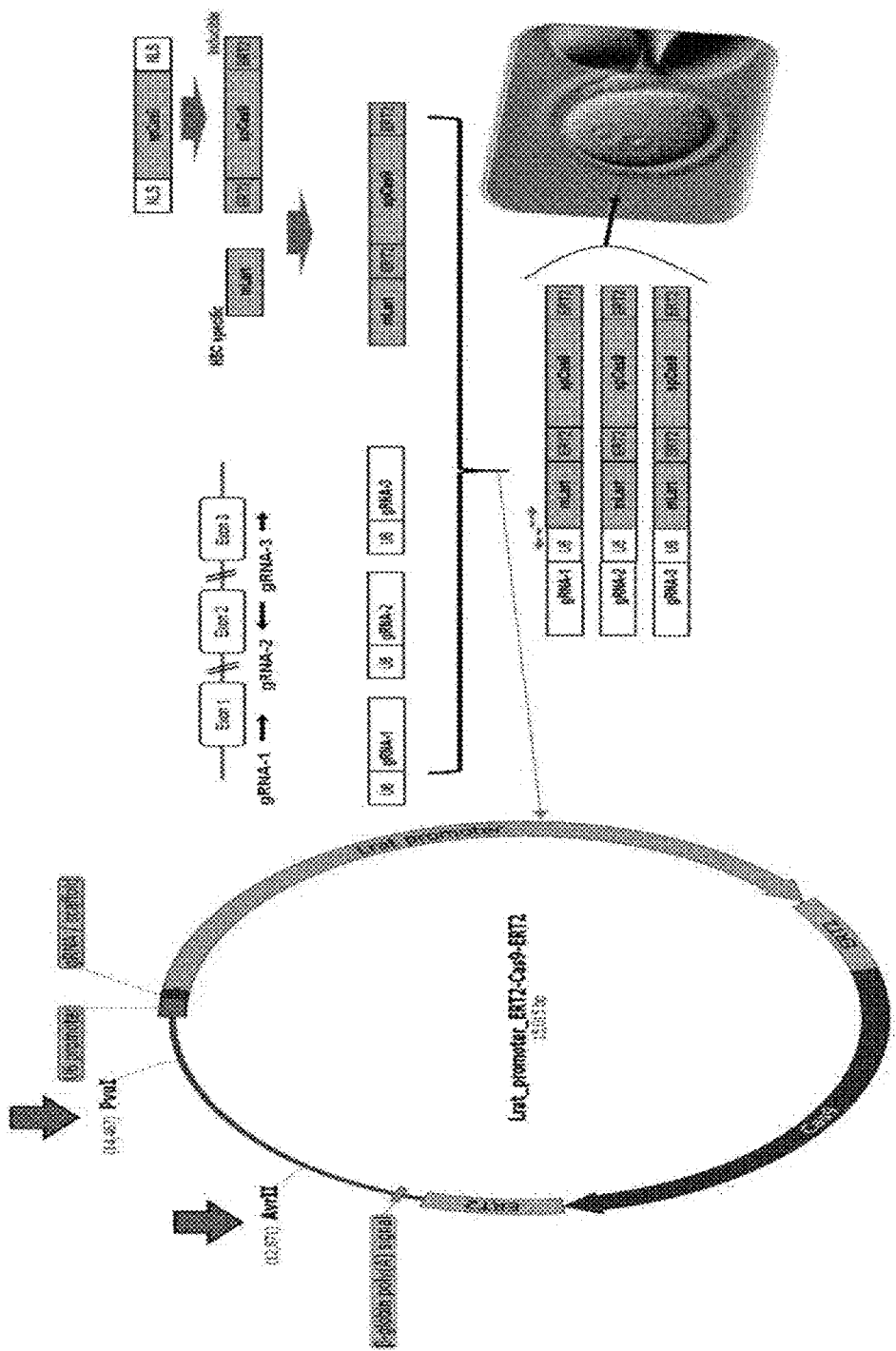
FIG. 5 illustrates DNA for microinjection, which is produced to microinject a recombinant vector according to an embodiment of the present invention into an embryo.

As one embodiment for the production of transgenic mice, as illustrated in FIG. 5, 3 DNAs (pLrat-ERT2Cas9ERT2-TIF1γ gRNAs) in which the regulation of liver fibrosis inhibitory gene (TIF1γ) expression is induced by tamoxifen were double-cut with AvrII/PvuI and linearized to be prepared for microinjection, and the 3 DNAs were microinjected into one cell-stage embryos at the same concentration. Standard microinjection procedures were used to produce such transgenic mice (Macrogen, Seoul, Korea).

A total of 4 ng/µl of a mixture of the 3 DNAs was directly injected into the pronucleus of a zygote using a micromanipulator, and embryos into which the DNA mixture was microinjected were incubated at 37° C. for 1 to 2 hours. 14 to 16 embryos were implanted into the fallopian tubes of pseudo-pregnant recipient mice (ICR) using a surgical method.

Transgenic mice produced in this manner were bred under conditions free of pathogens at Macrogen (Seoul, Korea), and all manipulations were carried out with the approval of the Experimental Animal Management Committee of Macrogen.

Example 4. Expression Analysis of DNA Modification-Inducing Protein Complex

Immunostaining was performed to confirm an expression pattern of the DNA modification-inducing protein complex according to the present invention. To this end, LX2 cells (Human hepatic stellate cell lines) were transfected therewith, and then treated with 1 nM tamoxifen (TMX), and after 4 hours, a decrease in a target gene (TIF1 gamma; TIF1γ) and an increase in an opposite gene (alpha SMA; α-SMA) according to whether or not TMX was treated were examined.

Figure 6A:
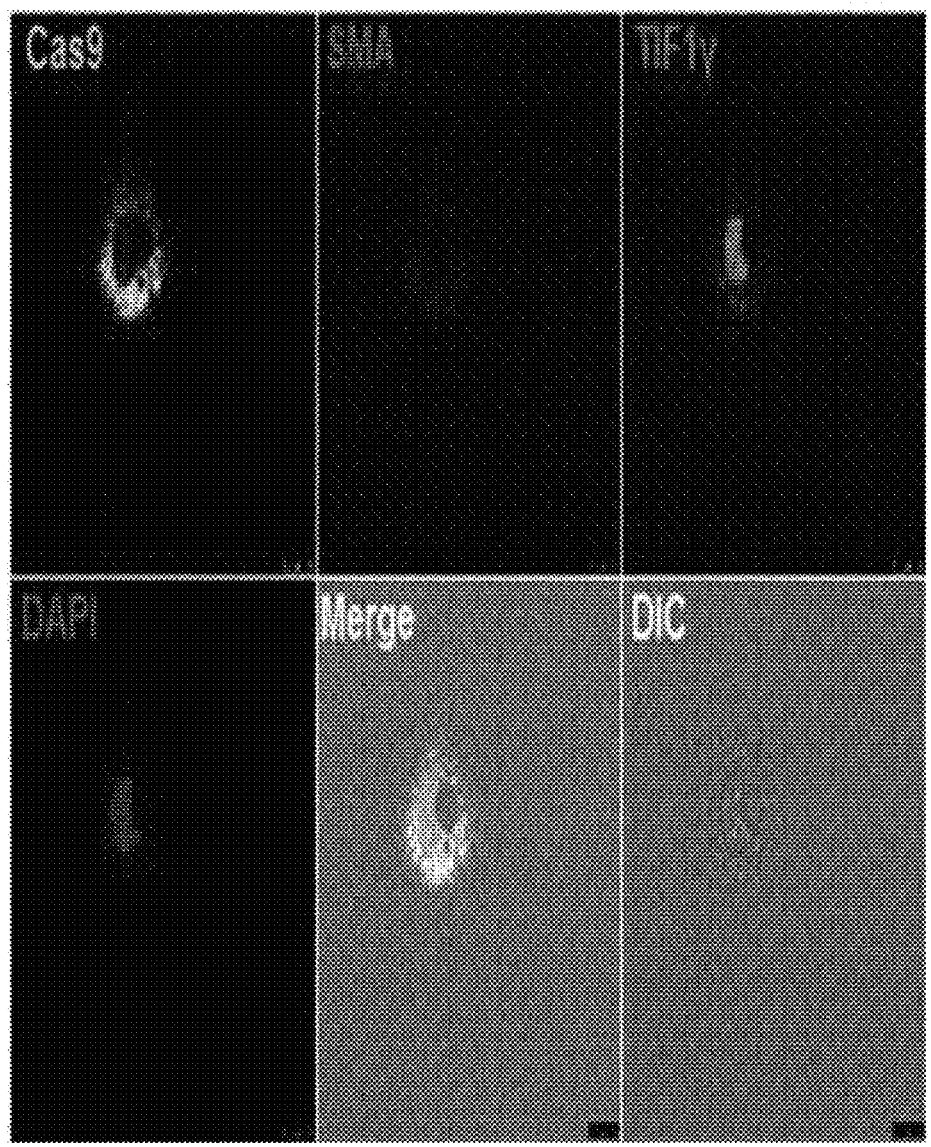
FIG. 6a illustrates the results of confirming the expression pattern of a Cas9-ERT2 protein complex when not treated with tamoxifen (TMX)
Figure 6B:
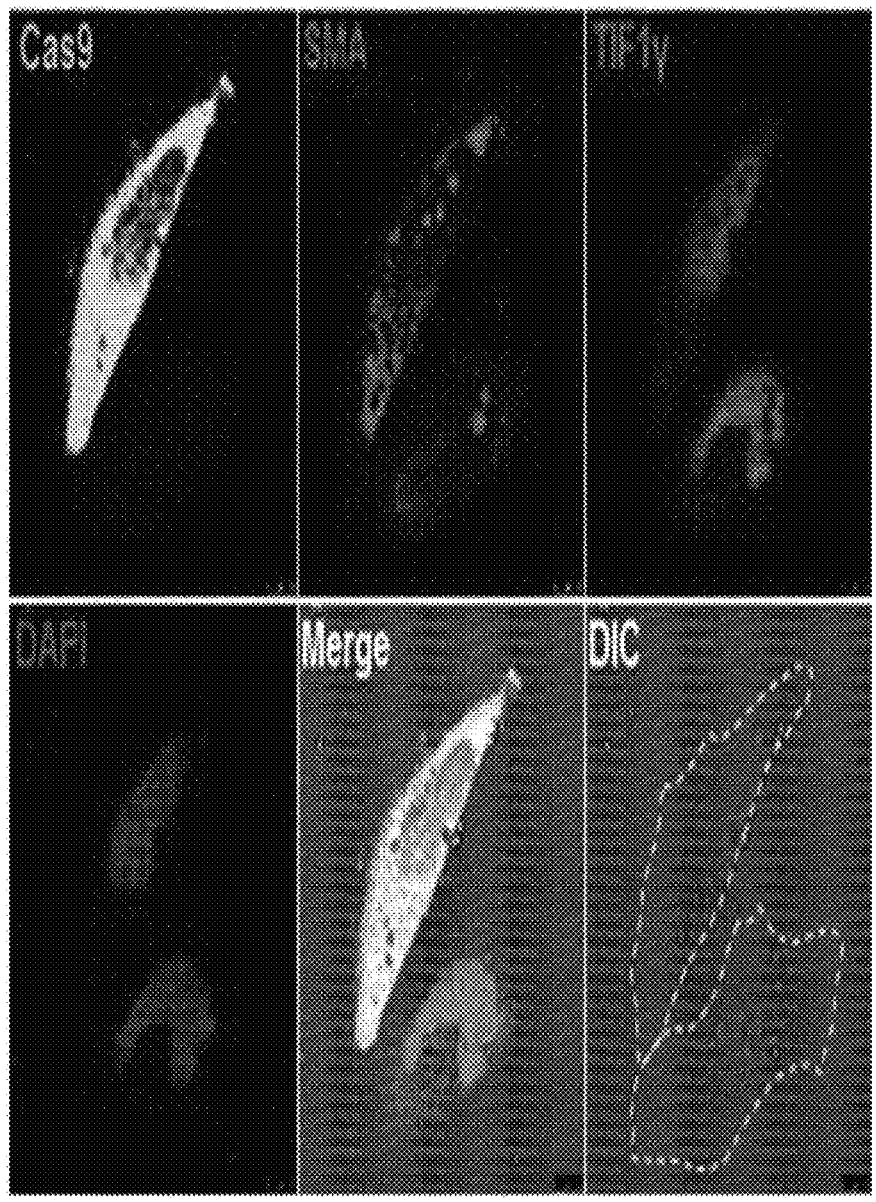
FIG. 6b illustrates the results of confirming the expression pattern of the Cas9-ERT2 protein complex when treated with TMX.

As a result, as illustrated in FIGS. 6a and 6b, when TMX was not treated, the transport of the Cas9-ERT2 protein complex expressed in the cytoplasm (cytosol) into the nucleus was inhibited, α-SMA was low, and TIF1γ was highly expressed in the nucleus (see FIG. 6a). In contrast, it was confirmed that, upon TMX treatment, the Cas9-ERT2 protein complex expressed in the cytoplasm was transported into the nucleus, α-SMA was high, and the expression of TIF1γ in the nucleus was reduced (see FIG. 6b).

Figure 7:
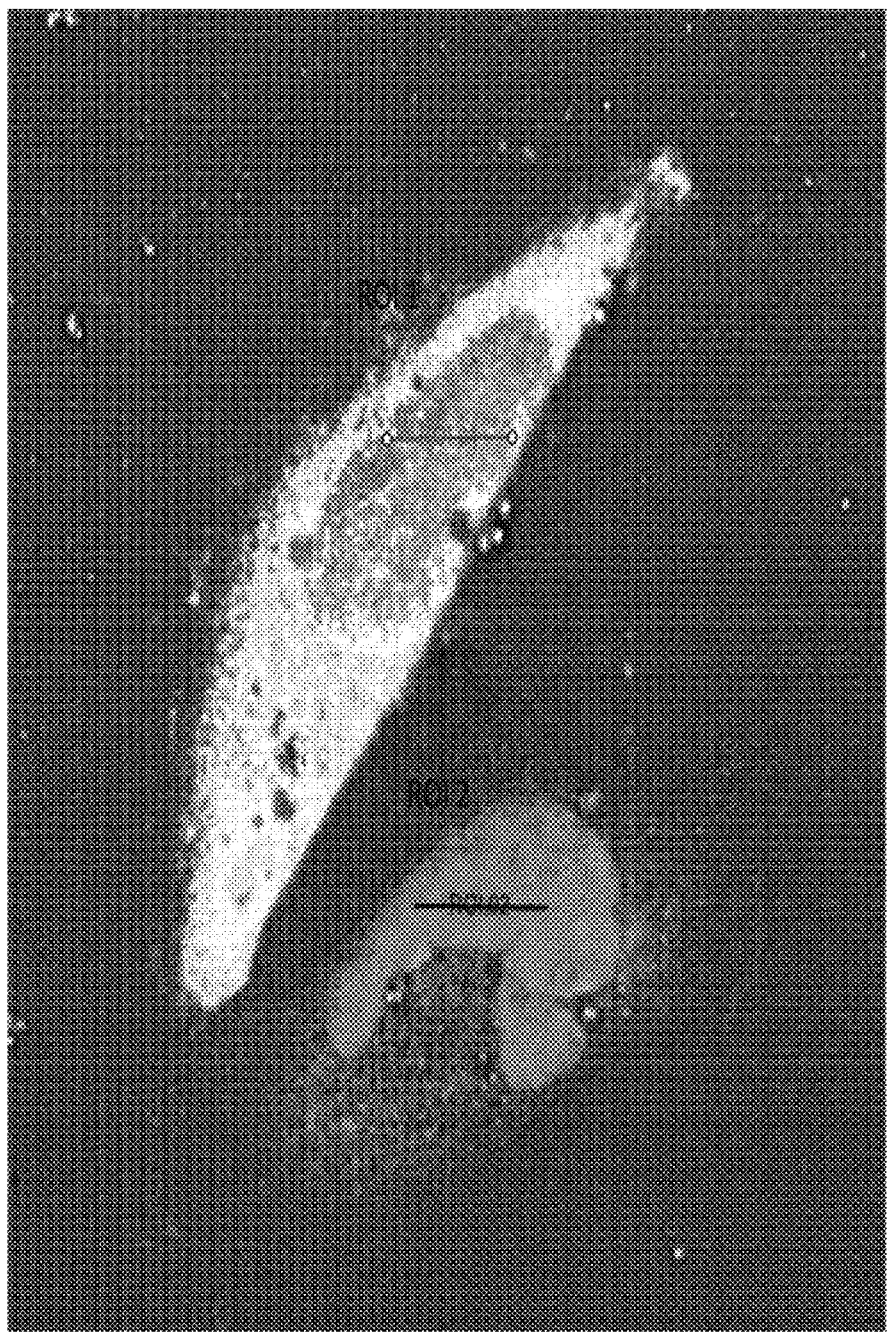
FIG. 7 illustrates the results of comparing ROI 1 (up cell) and ROI 2 (down cell), which is a cell on which vector transfection was not performed.
Figure 8:
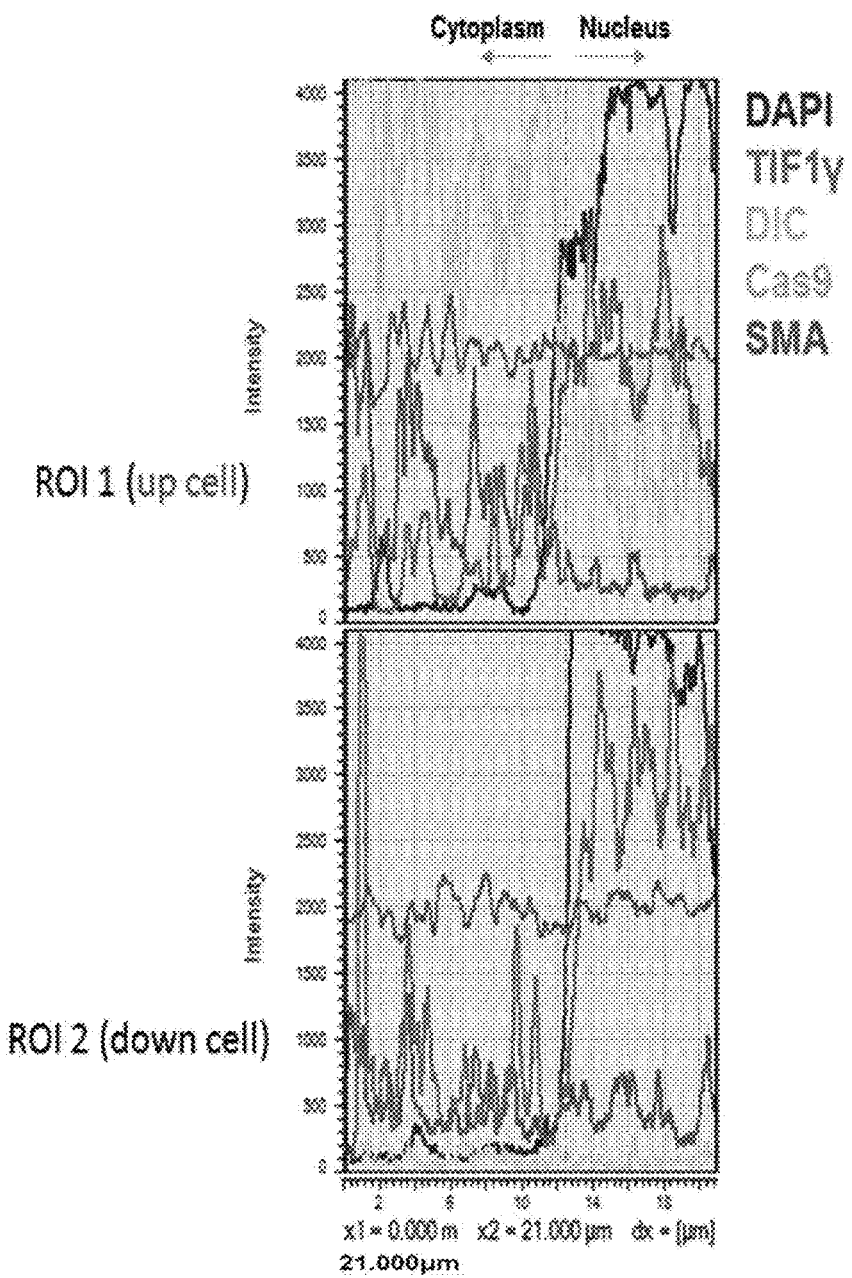
FIG. 8 illustrates the results of analyzing the expression patterns of ROI 1 and ROI 2 upon tamoxifen treatment according to intensity.

In addition, as a result of conducting analysis according to intensity using software, as illustrated in FIGS. 7 and 8, it was confirmed that, when comparing ROI 1 (up cell) and ROI 2 (down cell), which is a cell on which vector transfection was not performed (see FIG. 7), the Cas9-ERT2 protein complex expressed in the cytoplasm was transported into the nucleus by TMX treatment, intranuclear Cas9 was higher in ROI 1 than in ROI 2, α-SMA was high in the cytoplasm, and TIF1γ expression in the nucleus was reduced (see FIG. 8).

For reference, the sequence list of the present invention is shown in Table 3 below.

TABLE 3

| | |
|---|---|
| SEQ ID NO: 1 | Forward Primer |
| SEQ ID NO: 2 | Reverse Primer |
| SEQ ID NO: 3 | transcriptional intermediary factor 1 gamma gRNA 1 |
| SEQ ID NO: 4 | transcriptional intermediary factor 1 gamma gRNA 2 |
| SEQ ID NO: 5 | transcriptional intermediary factor 1 gamma gRNA 3 |
| SEQ ID NO: 6 | Cas9-ERT2 Forward Primer |
| SEQ ID NO: 7 | Cas9-ERT2 Reverse Primer |
| SEQ ID NO: 8 | transcriptional intermediary factor 1 gamma gRNA U6-F |

TABLE 3-continued

| | |
|---|---|
| SEQ ID NO: 9 | transcriptional intermediary factor 1 gamma gRNA gRNA1-R |
| SEQ ID NO: 10 | transcriptional intermediary factor 1 gamma gRNA gRNA2-R |
| SEQ ID NO: 11 | transcriptional intermediary factor 1 gamma gRNA gRNA3-R |
| SEQ ID NO: 12 | ERT2-Cas9-ERT2 |
| SEQ ID NO: 13 | RNA polymerase III promoter for human U6 snRNA |
| SEQ ID NO: 14 | human cytomegalovirus (CMV) immediate early promoter |
| SEQ ID NO: 15 | Cas9 (Csn1) endonuclease from the *Streptococcus pyogenes* Type II CRISPR/Cas system |

The foregoing description of the present invention is provided for illustrative purposes only, and it will be understood by those of ordinary skill in the art to which the present invention pertains that the present invention may be easily modified into other particular forms without changing the technical spirit or essential characteristics of the present invention. Thus, the above-described examples should be construed as being provided for illustrative purposes only and not for purposes of limitation.

INDUSTRIAL APPLICABILITY

A protein complex according to the present invention can modify specific DNA through guide RNA (gRNA) and also enables more precise DNA modification work at a desired time and a desired site by using a promoter of a gene that exhibits desired tissue- or cell-specific expression. Accordingly, the present invention is expected to be applied to develop new and convenient DNA modification techniques.

The invention claimed is:

1. A recombinant vector comprising: (a) a U6 promoter and a guide RNA (gRNA), and (b) a cytomegalovirus (CMV) promoter and a gene encoding a protein complex, wherein the protein complex is encoded by a gene consisting of the nucleotide sequence of SEQ ID NO: 12, and wherein the U6 promoter, the gRNA, the CMV promoter, and the gene consisting of SEQ ID No: 12 are operatively linked within the recombinant vector.

* * * * *